United States Patent
Hassler et al.

(10) Patent No.: US 12,383,415 B2
(45) Date of Patent: Aug. 12, 2025

(54) INTRA-ARTICULAR JOINT REPLACEMENT AND METHOD

(71) Applicant: Tornier SAS, Montbonnot-Saint-Martin (FR)

(72) Inventors: Michel Hassler, Saint Ismier (FR); Gilles Walch, Lyons (FR); Pierric Deransart, Saint Martin d'uriage (FR); Lucile Ferrand, Montbonnot (FR); Pascal Boileau, Nice (FR)

(73) Assignee: TORNIER SAS, Montbonnot-Saint-Martin (FR)

( * ) Notice: Subject to any disclaimer, the term of this patent is extended or adjusted under 35 U.S.C. 154(b) by 170 days.

(21) Appl. No.: 18/458,322

(22) Filed: Aug. 30, 2023

(65) Prior Publication Data
US 2023/0414379 A1    Dec. 28, 2023

Related U.S. Application Data

(60) Division of application No. 16/875,729, filed on May 15, 2020, now Pat. No. 11,771,568, which is a
(Continued)

(51) Int. Cl.
*A61F 2/40*    (2006.01)
*A61B 17/16*   (2006.01)
(Continued)

(52) U.S. Cl.
CPC ........ *A61F 2/4684* (2013.01); *A61B 17/1615* (2013.01); *A61B 17/1684* (2013.01);
(Continued)

(58) Field of Classification Search
CPC .......... A61F 2/40–2002/4096; A61B 17/1666; A61B 17/1684
See application file for complete search history.

(56) References Cited

U.S. PATENT DOCUMENTS 2,666,430 A    1/1954  Altamirano
3,412,733 A *  11/1968  Ross .................. A61B 17/1666
                                                        606/81
(Continued)

FOREIGN PATENT DOCUMENTS

CH    426096 A    12/1966
CH    507704 A    5/1971
(Continued)

OTHER PUBLICATIONS

"Aequalis-Fracture Shoulder Prosthesis—Surgical Technique," Tornier, Inc., in 32 pages.
(Continued)

*Primary Examiner* — Zade Coley
(74) *Attorney, Agent, or Firm* — DUANE MORRIS LLP (57) ABSTRACT

Methods of implanting a prosthesis to repair a joint include exposing a first bone of the joint; resecting an end portion of the first bone to form a resected end defining a resection plane; forming a concavity in the resected end portion of the first bone using a shaping tool, the concavity extending at least through a full hemispherical arc; selecting a diameter of the prosthesis to be implanted; and implanting a prosthesis having the selected diameter in the concavity.

10 Claims, 7 Drawing Sheets

Related U.S. Application Data continuation of application No. 15/224,188, filed on Jul. 29, 2016, now Pat. No. 10,695,195, which is a division of application No. 12/768,154, filed on Apr. 27, 2010, now Pat. No. 9,408,652.

(51) Int. Cl.
| | |
|---|---|
| A61B 17/88 | (2006.01) |
| A61B 90/92 | (2016.01) |
| A61F 2/46 | (2006.01) |
| A61B 90/00 | (2016.01) |
| A61F 2/30 | (2006.01) |

(52) U.S. Cl.
CPC ............ *A61B 17/885* (2013.01); *A61B 90/92* (2016.02); *A61F 2/4014* (2013.01); *A61B 2090/062* (2016.02); *A61F 2002/30616* (2013.01)

(56) References Cited

U.S. PATENT DOCUMENTS

| | | | |
|---|---|---|---|
| 3,694,820 A | 10/1972 | Scales et al. | |
| 3,815,157 A | 6/1974 | Skorecki et al. | |
| 3,842,442 A | 10/1974 | Kolbel | |
| 3,864,758 A | 2/1975 | Yakich | |
| 3,869,730 A | 3/1975 | Skobel | |
| 3,916,451 A * | 11/1975 | Buechel | A61F 2/3854 |
| | | | 403/56 |
| 3,938,193 A | 2/1976 | Sargunar | |
| 3,978,528 A | 9/1976 | Crep | |
| 3,979,778 A | 9/1976 | Stroot | |
| 3,992,726 A | 11/1976 | Freeman et al. | |
| 4,003,095 A | 1/1977 | Gristina | |
| 4,023,572 A * | 5/1977 | Weigand | A61B 17/1666 |
| | | | 606/81 |
| 4,030,143 A * | 6/1977 | Elloy | A61F 2/40 |
| | | | 623/19.12 |
| 4,040,131 A | 8/1977 | Gristina | |
| 4,054,955 A | 10/1977 | Seppo | |
| 4,126,924 A | 11/1978 | Akins et al. | |
| 4,131,116 A * | 12/1978 | Hedrick | A61B 17/1666 |
| | | | 606/81 |
| 4,135,517 A | 1/1979 | Reale | |
| 4,179,758 A | 12/1979 | Gristina | |
| 4,206,517 A | 6/1980 | Pappas et al. | |
| 4,261,062 A | 4/1981 | Amstutz et al. | |
| 4,479,271 A | 10/1984 | Bolesky et al. | |
| 4,550,450 A | 11/1985 | Kinnett | |
| 4,662,891 A * | 5/1987 | Noiles | A61F 2/4609 |
| | | | 623/22.25 |
| 4,693,723 A | 9/1987 | Gabard | |
| 4,822,370 A | 4/1989 | Schelhas | |
| 4,846,840 A | 7/1989 | Leclercq et al. | |
| 4,865,605 A | 9/1989 | Dines et al. | |
| 4,865,609 A | 9/1989 | Roche | |
| 4,892,549 A | 1/1990 | Figgie, III et al. | |
| 4,919,670 A | 4/1990 | Dale et al. | |
| 4,957,510 A | 9/1990 | Cremascoli | |
| 4,963,155 A | 10/1990 | Lazzeri et al. | |
| 4,964,865 A | 10/1990 | Burkhead et al. | |
| 5,030,233 A | 7/1991 | Ducheyne | |
| 5,032,132 A | 7/1991 | Matsen, III et al. | |
| 5,053,050 A | 10/1991 | Itay | |
| 5,080,673 A | 1/1992 | Burkhead et al. | |
| 5,080,685 A | 1/1992 | Bolesky et al. | |
| 5,127,920 A | 7/1992 | MacArthur | |
| 5,135,529 A | 8/1992 | Paxson et al. | |
| 5,163,961 A | 11/1992 | Harwin | |
| 5,181,928 A | 1/1993 | Bolesky et al. | |
| 5,192,329 A | 3/1993 | Christie et al. | |
| 5,201,882 A | 4/1993 | Paxson | |
| 5,206,925 A | 4/1993 | Nakazawa et al. | |
| 5,222,984 A | 6/1993 | Forte | |
| 5,261,914 A | 11/1993 | Warren | |
| 5,314,479 A | 5/1994 | Rockwood, Jr. et al. | |
| 5,314,487 A | 5/1994 | Schryver et al. | |
| 5,330,531 A | 7/1994 | Capanna | |
| 5,358,526 A | 10/1994 | Tornier | |
| 5,383,936 A | 1/1995 | Kubein-Meesenburg et al. | |
| 5,425,779 A | 6/1995 | Schlosser et al. | |
| 5,435,722 A * | 7/1995 | Mandell | A61C 1/052 |
| | | | 433/165 |
| 5,443,515 A | 8/1995 | Cohen et al. | |
| 5,443,519 A | 8/1995 | Averill et al. | |
| 5,462,563 A | 10/1995 | Shearer et al. | |
| 5,507,817 A | 4/1996 | Craig et al. | |
| 5,507,818 A | 4/1996 | McLaughlin | |
| 5,507,819 A | 4/1996 | Wolf | |
| 5,507,824 A | 4/1996 | Lennox | |
| 5,534,033 A | 7/1996 | Simpson | |
| 5,549,682 A | 8/1996 | Roy | |
| 5,571,203 A | 11/1996 | Masini | |
| 5,580,352 A | 12/1996 | Sekel | |
| 5,702,447 A | 12/1997 | Walch et al. | |
| 5,702,457 A * | 12/1997 | Walch | A61F 2/4014 |
| | | | 623/19.13 |
| 5,702,486 A | 12/1997 | Craig et al. | |
| 5,723,018 A * | 3/1998 | Cyprien | A61F 2/40 |
| | | | 623/19.13 |
| 5,728,161 A | 3/1998 | Camino et al. | |
| 5,741,335 A | 4/1998 | Gerber et al. | |
| 5,755,719 A * | 5/1998 | Frieze | A61B 17/1666 |
| | | | 606/81 |
| 5,755,807 A | 5/1998 | Anstaett et al. | |
| 5,779,709 A | 7/1998 | Harris, Jr. et al. | |
| 5,800,551 A | 9/1998 | Williamson et al. | |
| 5,800,557 A | 9/1998 | Elhami | |
| 5,879,355 A * | 3/1999 | Ullmark | A61F 2/4601 |
| | | | 606/92 |
| 5,879,405 A | 3/1999 | Ries et al. | |
| 5,902,340 A | 5/1999 | White et al. | |
| 5,910,171 A | 6/1999 | Kummer et al. | |
| 5,928,285 A | 7/1999 | Bigliani et al. | |
| 5,941,706 A * | 8/1999 | Ura | A61C 3/02 |
| | | | 433/165 |
| 5,944,758 A | 8/1999 | Mansat et al. | |
| 5,961,555 A | 10/1999 | Huebner | |
| 5,972,368 A | 10/1999 | McKay | |
| 5,984,927 A | 11/1999 | Wenstrom, Jr. et al. | |
| 6,015,437 A | 1/2000 | Stossel | |
| 6,027,503 A * | 2/2000 | Khalili | A61B 17/1666 |
| | | | 606/81 |
| 6,033,439 A | 3/2000 | Camino et al. | |
| 6,045,302 A * | 4/2000 | Orr | B23B 51/0426 |
| | | | 408/83 |
| 6,045,582 A | 4/2000 | Prybyla | |
| 6,045,583 A | 4/2000 | Gross et al. | |
| 6,090,145 A * | 7/2000 | Hassler | A61F 2/30721 |
| | | | 623/23.14 |
| 6,096,084 A | 8/2000 | Townley | |
| 6,102,953 A | 8/2000 | Huebner | |
| 6,129,764 A | 10/2000 | Servidio | |
| 6,165,224 A | 12/2000 | Tornier | |
| 6,171,341 B1 | 1/2001 | Boileau et al. | |
| 6,197,062 B1 | 3/2001 | Fenlin | |
| 6,197,063 B1 | 3/2001 | Dews | |
| 6,203,575 B1 | 3/2001 | Farey | |
| 6,206,925 B1 | 3/2001 | Tornier | |
| 6,221,076 B1 * | 4/2001 | Albrektsson | A61B 17/1666 |
| | | | 407/62 |
| 6,228,120 B1 | 5/2001 | Leonard et al. | |
| 6,245,074 B1 * | 6/2001 | Allard | A61B 17/1684 |
| | | | 606/80 |
| 6,267,767 B1 | 7/2001 | Strobel et al. | |
| 6,283,999 B1 * | 9/2001 | Rockwood, Jr. | A61F 2/40 |
| | | | 623/19.12 |
| 6,312,467 B1 | 11/2001 | McGee | |
| 6,334,874 B1 | 1/2002 | Tornier et al. | |
| 6,364,910 B1 | 4/2002 | Shultz et al. | |
| 6,368,352 B1 | 4/2002 | Camino et al. | |
| 6,368,353 B1 | 4/2002 | Arcand | |

(56) References Cited

U.S. PATENT DOCUMENTS

| | | |
|---|---|---|
| 6,383,227 B1 | 5/2002 | Baroud et al. |
| 6,398,812 B1 | 6/2002 | Masini |
| 6,406,495 B1 | 6/2002 | Schoch |
| 6,406,496 B1 | 6/2002 | Rüter |
| 6,436,144 B1 | 8/2002 | Ahrens |
| 6,436,146 B1 * | 8/2002 | Hassler .................. A61F 2/4261 623/18.11 |
| 6,436,147 B1 | 8/2002 | Zweymüller |
| 6,454,811 B1 | 9/2002 | Sherwood et al. |
| 6,458,136 B1 | 10/2002 | Allard et al. |
| 6,475,221 B1 * | 11/2002 | White .................. A61B 17/1666 404/54 |
| 6,475,243 B1 | 11/2002 | Sheldon et al. |
| 6,494,913 B1 | 12/2002 | Huebner |
| 6,506,214 B1 | 1/2003 | Gross |
| 6,508,840 B1 | 1/2003 | Rockwood, Jr. et al. |
| 6,511,511 B1 | 1/2003 | Slivka et al. |
| 6,514,287 B2 | 2/2003 | Ondrla et al. |
| 6,520,994 B2 | 2/2003 | Nogarin |
| 6,530,957 B1 | 3/2003 | Jack |
| 6,541,022 B1 | 4/2003 | Murphy et al. |
| 6,558,425 B2 | 5/2003 | Rockwood, Jr. |
| 6,569,202 B2 | 5/2003 | Whiteside |
| 6,589,281 B2 | 7/2003 | Hyde, Jr. |
| 6,605,117 B2 | 8/2003 | Kuberasampath et al. |
| 6,620,197 B2 | 9/2003 | Maroney et al. |
| 6,626,946 B1 | 9/2003 | Walch et al. |
| 6,673,114 B2 | 1/2004 | Hartdegen et al. |
| 6,673,115 B2 | 1/2004 | Resch et al. |
| 6,679,916 B1 | 1/2004 | Frankle et al. |
| 6,692,563 B2 | 2/2004 | Zimmermann |
| 6,730,252 B1 | 5/2004 | Teoh et al. |
| 6,736,851 B2 | 5/2004 | Maroney et al. |
| 6,746,487 B2 | 6/2004 | Scifert et al. |
| 6,749,637 B1 | 6/2004 | Bähler |
| 6,755,866 B2 | 6/2004 | Southworth |
| 6,761,740 B2 | 7/2004 | Tornier |
| 6,767,928 B1 | 7/2004 | Murphy et al. |
| 6,780,190 B2 | 8/2004 | Maroney |
| 6,783,549 B1 * | 8/2004 | Stone .................. A61B 17/1684 623/18.11 |
| 6,790,234 B1 * | 9/2004 | Frankle .................. A61F 2/40 623/19.12 |
| 6,797,006 B2 | 9/2004 | Hodorek |
| 6,863,690 B2 | 3/2005 | Ball et al. |
| 6,875,234 B2 | 4/2005 | Lipman et al. |
| 6,887,277 B2 | 5/2005 | Rauscher et al. |
| 6,890,358 B2 | 5/2005 | Ball et al. |
| 6,902,584 B2 | 6/2005 | Kwan et al. |
| 6,942,699 B2 | 9/2005 | Stone et al. |
| 6,953,478 B2 | 10/2005 | Bouttens et al. |
| 6,969,406 B2 | 11/2005 | Tornier |
| 7,011,686 B2 * | 3/2006 | Ball .................. A61F 2/4014 623/19.14 |
| 7,033,395 B2 | 4/2006 | Cauthen |
| 7,051,417 B2 | 5/2006 | Michelson |
| 7,066,959 B2 | 6/2006 | Errico et al. |
| 7,108,719 B2 | 9/2006 | Horber |
| 7,166,132 B2 | 1/2007 | Callaway et al. |
| 7,169,184 B2 | 1/2007 | Dalla Pria |
| 7,175,663 B1 | 2/2007 | Stone |
| 7,195,645 B2 | 3/2007 | DiSilvestro et al. |
| 7,238,207 B2 | 7/2007 | Blatter et al. |
| 7,238,208 B2 | 7/2007 | Camino et al. |
| 7,250,550 B2 | 7/2007 | Overby et al. |
| 7,297,163 B2 | 11/2007 | Huebner |
| 7,309,360 B2 | 12/2007 | Tornier et al. |
| 7,329,284 B2 | 2/2008 | Maroney et al. |
| 7,338,498 B2 | 3/2008 | Long et al. |
| 7,338,528 B2 | 3/2008 | Stone et al. |
| 7,462,197 B2 * | 12/2008 | Tornier .................. A61F 2/4081 623/19.12 |
| 7,520,898 B2 * | 4/2009 | Re .................. A61B 17/1714 623/13.14 |
| 7,604,637 B2 * | 10/2009 | Johnson .................. A61F 2/30724 606/81 |
| 8,062,376 B2 * | 11/2011 | Shultz .................. A61F 2/40 623/19.12 |
| 8,366,713 B2 * | 2/2013 | Long .................. A61B 17/1675 606/80 |
| 8,414,586 B2 * | 4/2013 | Cawthan .................. A61B 17/1666 606/81 |
| 8,864,834 B2 | 10/2014 | Boileau et al. |
| 8,974,536 B2 | 3/2015 | Walch et al. |
| 9,089,435 B2 | 7/2015 | Walch et al. |
| 9,408,652 B2 | 8/2016 | Hassler et al. |
| 10,251,755 B2 | 4/2019 | Boileau et al. |
| 10,413,416 B2 | 9/2019 | Boileau et al. |
| 10,695,195 B2 | 6/2020 | Hassler et al. |
| 2001/0032021 A1 | 10/2001 | McKinnon |
| 2001/0047210 A1 | 11/2001 | Wolf |
| 2001/0049561 A1 | 12/2001 | Dews et al. |
| 2002/0032484 A1 | 3/2002 | Hyde, Jr. |
| 2002/0099381 A1 | 7/2002 | Maroney |
| 2002/0138148 A1 | 9/2002 | Hyde, Jr. |
| 2002/0143402 A1 | 10/2002 | Steinberg |
| 2002/0151982 A1 | 10/2002 | Masini |
| 2002/0177901 A1 | 11/2002 | Howie |
| 2003/0009171 A1 | 1/2003 | Tornier |
| 2003/0065397 A1 * | 4/2003 | Hanssen .................. A61F 2/34 623/23.23 |
| 2003/0097183 A1 | 5/2003 | Rauscher et al. |
| 2003/0114933 A1 | 6/2003 | Bouttens et al. |
| 2003/0125809 A1 | 7/2003 | Iannotti et al. |
| 2003/0149485 A1 | 8/2003 | Tornier |
| 2003/0158605 A1 | 8/2003 | Tornier |
| 2003/0181916 A1 * | 9/2003 | Wolford .................. A61B 17/1666 606/81 |
| 2004/0002765 A1 * | 1/2004 | Maroney .................. A61F 2/4014 623/19.12 |
| 2004/0006392 A1 | 1/2004 | Grusin et al. |
| 2004/0030394 A1 * | 2/2004 | Horber .................. A61F 2/4014 623/19.12 |
| 2004/0034431 A1 | 2/2004 | Maroney et al. |
| 2004/0064189 A1 * | 4/2004 | Maroney .................. A61F 2/30734 623/19.13 |
| 2004/0064190 A1 | 4/2004 | Ball et al. |
| 2004/0068320 A1 | 4/2004 | Robie et al. |
| 2004/0133276 A1 | 7/2004 | Lang et al. |
| 2004/0138754 A1 | 7/2004 | Lang et al. |
| 2004/0148033 A1 | 7/2004 | Schroeder |
| 2004/0193168 A1 * | 9/2004 | Long .................. A61B 17/1684 606/80 |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0210317 A1 | 10/2004 | Maroney et al. |
| 2004/0220673 A1 | 11/2004 | Pria |
| 2004/0220674 A1 | 11/2004 | Pria |
| 2004/0225367 A1 | 11/2004 | Glien et al. |
| 2004/0230197 A1 | 11/2004 | Tornier et al. |
| 2004/0249383 A1 * | 12/2004 | White .................. A61B 17/1666 606/80 |
| 2004/0267370 A1 | 12/2004 | Ondrla |
| 2005/0008672 A1 | 1/2005 | Winterbottom et al. |
| 2005/0010304 A1 | 1/2005 | Jamali |
| 2005/0015154 A1 | 1/2005 | Lindsey et al. |
| 2005/0033443 A1 | 2/2005 | Blatter et al. |
| 2005/0043805 A1 | 2/2005 | Chudik |
| 2005/0049709 A1 | 3/2005 | Tornier |
| 2005/0060039 A1 | 3/2005 | Cyprien |
| 2005/0065612 A1 | 3/2005 | Winslow |
| 2005/0085919 A1 | 4/2005 | Durand-Allen et al. |
| 2005/0085921 A1 | 4/2005 | Gupta et al. |
| 2005/0090902 A1 | 4/2005 | Masini |
| 2005/0107882 A1 | 5/2005 | Stone et al. |
| 2005/0113837 A1 * | 5/2005 | Salyer .................. A61B 17/1666 606/80 |
| 2005/0113931 A1 | 5/2005 | Horber |
| 2005/0119531 A1 | 6/2005 | Sharratt |
| 2005/0143818 A1 | 6/2005 | Yuan et al. |
| 2005/0143829 A1 | 6/2005 | Ondrla et al. |

(56) References Cited

U.S. PATENT DOCUMENTS

| | | |
|---|---|---|
| 2005/0159751 A1* | 7/2005 | Berthusen ............ A61B 17/1666 606/80 |
| 2005/0165490 A1 | 7/2005 | Tornier |
| 2005/0177241 A1 | 8/2005 | Angibaud et al. |
| 2005/0186247 A1 | 8/2005 | Hunter et al. |
| 2005/0197708 A1 | 9/2005 | Stone et al. |
| 2005/0209700 A1 | 9/2005 | Rockwood, Jr. et al. |
| 2005/0216092 A1 | 9/2005 | Marik et al. |
| 2005/0240267 A1 | 10/2005 | Randall et al. |
| 2005/0245934 A1 | 11/2005 | Tuke et al. |
| 2005/0251263 A1 | 11/2005 | Forrer et al. |
| 2005/0256584 A1 | 11/2005 | Farrar |
| 2005/0267590 A1 | 12/2005 | Lee |
| 2005/0278030 A1 | 12/2005 | Tornier et al. |
| 2005/0278031 A1 | 12/2005 | Tornier et al. |
| 2005/0278032 A1 | 12/2005 | Tornier et al. |
| 2005/0278033 A1 | 12/2005 | Tornier et al. |
| 2005/0288681 A1 | 12/2005 | Klotz et al. |
| 2005/0288791 A1 | 12/2005 | Tornier et al. |
| 2006/0004462 A1 | 1/2006 | Gupta |
| 2006/0009852 A1 | 1/2006 | Winslow et al. |
| 2006/0020344 A1 | 1/2006 | Shultz et al. |
| 2006/0025796 A1 | 2/2006 | Merced-O |
| 2006/0030946 A1 | 2/2006 | Ball et al. |
| 2006/0111787 A1* | 5/2006 | Bailie ................... A61F 2/4081 623/908 |
| 2006/0122705 A1* | 6/2006 | Morgan ................ A61F 2/4081 623/19.11 |
| 2006/0195110 A1* | 8/2006 | White ................ A61B 17/1684 606/81 |
| 2006/0235539 A1* | 10/2006 | Blunn ................ A61B 17/1666 623/23.11 |
| 2006/0241775 A1 | 10/2006 | Buss |
| 2007/0078516 A1 | 4/2007 | Emami |
| 2007/0142916 A1 | 6/2007 | Olson, Jr. et al. |
| 2007/0156250 A1 | 7/2007 | Seitz, Jr. et al. |
| 2007/0173945 A1 | 7/2007 | Wiley et al. |
| 2007/0179562 A1 | 8/2007 | Nycz |
| 2007/0198087 A1 | 8/2007 | Coleman et al. |
| 2007/0225817 A1 | 9/2007 | Reubelt et al. |
| 2007/0225818 A1 | 9/2007 | Reubelt et al. |
| 2007/0225821 A1 | 9/2007 | Reubelt et al. |
| 2007/0244564 A1 | 10/2007 | Ferrand et al. |
| 2007/0250174 A1 | 10/2007 | Tornier et al. |
| 2007/0276509 A1 | 11/2007 | Ratcliffe et al. |
| 2008/0183297 A1* | 7/2008 | Boileau ............... A61B 17/1637 623/16.11 |
| 2009/0125113 A1 | 5/2009 | Guederian et al. |
| 2009/0270993 A1* | 10/2009 | Maisonneuve .... A61B 17/1778 623/19.14 |
| 2009/0287309 A1* | 11/2009 | Walch ................ A61B 17/1739 623/18.11 |
| 2009/0292364 A1* | 11/2009 | Linares ................ A61B 17/686 623/19.13 |
| 2009/0306782 A1* | 12/2009 | Schwyzer ............. A61F 2/4003 623/19.12 |
| 2010/0280517 A1* | 11/2010 | Cawthan ............. A61B 17/1666 606/81 |
| 2010/0280518 A1* | 11/2010 | Gary .................. A61B 17/1666 606/84 |
| 2011/0098822 A1 | 4/2011 | Walch et al. |
| 2011/0166661 A1 | 7/2011 | Boileau et al. |
| 2011/0213372 A1* | 9/2011 | Keefer ................ A61B 17/1735 606/85 |
| 2011/0264153 A1 | 10/2011 | Hassler et al. |
| 2014/0058523 A1 | 2/2014 | Walch et al. |
| 2015/0297354 A1 | 10/2015 | Walch et al. |
| 2019/0358045 A1 | 11/2019 | Boileau et al. |

FOREIGN PATENT DOCUMENTS

| | | |
|---|---|---|
| DE | 1950937 U | 12/1966 |
| DE | 19630298 A1 | 1/1998 |
| EP | 0257359 B1 | 11/1991 |
| EP | 0299889 B1 | 3/1992 |
| EP | 0524857 A1 | 1/1993 |
| EP | 0617934 A1 | 10/1994 |
| EP | 0549480 B1 | 8/1997 |
| EP | 0599429 B1 | 10/1997 |
| EP | 0797964 A1 | 10/1997 |
| EP | 0679375 B1 | 9/1998 |
| EP | 0864306 A2 | 9/1998 |
| EP | 0712617 B1 | 9/1999 |
| EP | 0715836 B1 | 10/2001 |
| EP | 0664108 B1 | 8/2002 |
| EP | 0809986 B1 | 10/2002 |
| EP | 0927548 B1 | 5/2003 |
| EP | 0807426 B1 | 10/2003 |
| EP | 1062923 B1 | 1/2004 |
| EP | 1380274 A1 | 1/2004 |
| EP | 0903128 B1 | 5/2004 |
| EP | 1195149 B1 | 7/2005 |
| EP | 1064890 B1 | 9/2005 |
| EP | 1477120 B1 | 2/2007 |
| EP | 0903127 B1 | 6/2007 |
| EP | 1570816 B1 | 2/2008 |
| EP | 1652482 B1 | 3/2008 |
| EP | 1607069 B1 | 12/2009 |
| EP | 1402853 B1 | 5/2010 |
| EP | 1402854 B1 | 7/2010 |
| EP | 1323395 B1 | 8/2016 |
| EP | 1952771 B1 | 10/2016 |
| EP | 1952788 B1 | 2/2018 |
| EP | 3335676 A1 | 6/2018 |
| FR | 2248820 B1 | 6/1976 |
| FR | 2216981 B1 | 5/1979 |
| FR | 2574283 B1 | 9/1989 |
| FR | 2545352 B1 | 1/1990 |
| FR | 2699400 B1 | 2/1995 |
| FR | 2704747 B1 | 7/1995 |
| FR | 2726994 B1 | 4/1997 |
| FR | 2737107 B1 | 9/1997 |
| FR | 2652498 B1 | 12/1997 |
| FR | 2664809 B1 | 12/1997 |
| FR | 2721200 B1 | 9/1999 |
| FR | 2835425 B1 | 4/2004 |
| FR | 2836039 B1 | 10/2004 |
| SU | 749392 A1 | 7/1980 |
| WO | 1991007932 A1 | 6/1991 |
| WO | 1993009733 A1 | 5/1993 |
| WO | 1996017553 A1 | 6/1996 |
| WO | 1998046172 A1 | 10/1998 |
| WO | 1999049792 A1 | 10/1999 |
| WO | 1999065413 A1 | 12/1999 |
| WO | 2000015154 A1 | 3/2000 |
| WO | 2000041653 A1 | 7/2000 |
| WO | 2000062718 A1 | 10/2000 |
| WO | 2001047442 A1 | 7/2001 |
| WO | 2002039931 A1 | 5/2002 |
| WO | 2002039933 A1 | 5/2002 |
| WO | 2002049516 A1 | 6/2002 |
| WO | 2002067821 A2 | 9/2002 |
| WO | 2003005933 A2 | 1/2003 |
| WO | 2003092513 A1 | 11/2003 |
| WO | 2003094806 A1 | 11/2003 |
| WO | 2006039483 A2 | 4/2006 |
| WO | 2007109291 A2 | 9/2007 |
| WO | 2007109319 A2 | 9/2007 |
| WO | 2007109340 A2 | 9/2007 |
| WO | 2008015724 A2 | 2/2008 |

OTHER PUBLICATIONS

"Aequalis-Fracture Suture Technique in 5 Steps," Tornier, Inc., in 2 pages.
"Aequalis-Glenoid Keeled and Pegged—Surgical Technique," Tornier, Inc., in 12 pages.
"Aequalis Press-Fit Shoulder Prosthesis—Surgical Technique," Tornier, Inc., in 27 pages.
"Aequalis Resurfacing Head", retrieved from http://www.tornier-us.com/upper/shoulder/shorec004/index.php?pop+1 on Apr. 14, 2010.

(56) References Cited

OTHER PUBLICATIONS

"Aequalis-Reversed™ Shoulder Prosthesis, Surgical Technique," Tornier, Inc., in 24 pages.
"Anatomic Glenoid, Surgical Technique," Smith & Nephew, Inc., Feb. 2000 in 6 pages.
"Anatomical Shoulder™—Cemented Shoulder Prosthesis Product Information and Surgical Technique," Sulzer Medica, 2000, in 30 paqes.
"Anatomical Shoulder™ System—The new removable head option," Zimmer Inc., 2004 in 6 paqes.
"Anatomical Shoulder™ System Surgical Technique—Removable head option for improved surgical results," Zimmer, Inc., 2004, in 33 paqes.
Apoil, A., "A Condyle for the Rotator Cuff Muscles: The Total Shoulder Prosthesis," Aesculap—ICP S.A., Feb. 1994, in 4 paqes.
Bigliani/Flatow®—The Complete Shoulder Solution, Designed by Shoulder Surgeons for Shoulder Surgery, Zimmer, Inc., 2001 in 6 paqes.
"Bigliani/Flatow®—The Complete Shoulder Solution, Total Shoulder Arthroplasty Surgical Technique," Zimmer, Inc., 2003, in 30 paqes.
Bigliani/Flatow®—The Complete Shoulder Solution, 4-Part Fracture of the Humerus Surgical Technique, Zimmer, Inc., 2001.
"Bio-Modular®/ Bi-Polar Shoulder Arthroplasty," Biomet, Inc., 1997, in 2 pages.
"Bio-Modular® Choice—Shoulder System—Surgical Technique," Biomet Orthopedics, Inc., 2004, in 16 paqes.
"Bio-Modular Total Shoulder Surgical Technique," Biomet Orthopedics, Inc., 2001.
Boileau, P., et al. "Adaptability and modularity of shoulder prosthese," Maitrise Orthopedique, https://www.maitriseorthop.com/corpusmaitri/orthopaedic/prothese_epaule_orthop/boileau_u s.shtml, downloaded Jan. 3, 2006.
Boileau, P., et al. "Arthroscopic Repair of Full-Thickness Tears of the Supraspinatus: Does the Tendon Really Heal?" The Journal of Bone and Joint Surgery, Inc., Jun. 2005, 87A(6): 1229-1240.
Buechel, F.F., "Buechel-Pappas™ Modular Salvage Shoulder System, Surgical Procedure," Endotec, Inc., Aug. 2001, in 8 pages.
Buechel, F.F., "Buechel-Pappas™ Resurfacing Shoulder System, Surgical Procedure" Endotec, Inc., Aug. 2000, in 8 paqes.
Buechel, F.F., "Buechel-Pappas™ Total Shoulder System, Surgical Procedure," Endotec, Inc., Aug. 2000, in 16 pages.
Cofield, R.H., "Cofield2 Total Shoulder System, Surgical Technique," Smith & Nephew, 1997, in 32 pages.
"Copeland™ Humeral Resurfacing Head," Biomet Orthopedics, Inc., 2001, in 12 pages.
"Delta CTA™ Reverse Shoulder Prosthesis—Surgical Technique," DePuy International Ltd., revised Aug. 2004, in 28 pages.
"Design Rationale," Latitude® Total Elbow, pp. 3-38.
Fenlin, Jr., J.M., "Total Glenohumeral Joint Replacement," Symposium on Surgery of the Shoulder, Orthopedic Clinics of North America, Apr. 1975, 6(2): 565-583.
"Global C.A.P. TM Surgical Technique, Resurfacing Humeral Head Implant," DePuy International, Ltd., revised Oct. 2004, in 23 pages.
Hertel, R., "Technical considerations for implantation of Epoca glenoid components (Leseprobe)," Epoca Newsletter, May 14, 2001, in 1 page.
Klein, T.J., et al., "Mechanically Favorable Bone Remodeling in Rotator Cuff Arthropathy Patients with Good Function," Minneapolis Sports Medicine Center and University of Minnesota, in 2 paqes.
Mansat, M., "Neer 3™, Surgical Technique for Fractures," Smith & Nephew, Sep. 2000, in 19 pages.
Nicholson, G.P., "Chapter 7: Arthroplasty and Rotator Cuff Deficiency," Shoulder Arthroplasty, 2005, DD. 149-166.
"Offset Head: Bio-Modular® Total Shoulder," Biomet, Inc. 2000 in 2 pages.
"The Foundation® Total Shoulder System," Encore Surgical, in 2 pages.
"The Townley Modular Shoulder—Design by Reason," Biopro, Inc., in 2 pages.
"Tornier Surgical Technique Addendum, Tornier Aequalis® Reversed Hemi-Adaptor Technique," Tornier, Inc., Aug. 8, 2005.
"Tornier Surgical Technique Addendum, Aequalis® Reversed Shoulder Polyethylene Insert," Tornier, Inc., Oct. 8, 2005, in 1 page.
"Zimmer® Shoulder Retractors," Zimmer, Inc., 2000, in 2 pages.
On-Final Office Action issued in connection with U.S. Appl. No. 14/754,506, Jul. 19, 2022, 9 pages.
Final Office Action issued in connection with U.S. Appl. No. 14/574,506, Mar. 18, 2022, 15 pages.
Non-Final Office Action issued in connection with U.S. Appl. No. 14/754,506, Sep. 23, 2021, 11 pages.

\* cited by examiner

INTRA-ARTICULAR JOINT REPLACEMENT AND METHOD

CROSS REFERENCE TO RELATED APPLICATIONS

This application is a divisional of a co-pending U.S. patent Application Ser. No. 16/875,729, filed on May 15, 2020, which is a continuation of U.S. patent application Ser. No. 15/224,188, filed on Jul. 29, 2016 (U.S. Pat. No. 10,695,195), which is a divisional of U.S. patent application Ser. No. 12/768,154, filed on Apr. 27, 2010 (U.S. Pat. No. 9,408,652), which are all hereby incorporated by reference in their entirety.

BACKGROUND

One type of method used to replace damaged joints (e.g., shoulder joints) is interpositional arthroplasty. The method of interpositional arthroplasty uses tissue from the patient or an artificial replacement to repair a damaged or malformed joint. An interpositional implant is positioned at the joint to act as an engagement surface between two adjacent bone structures to allow articular movement.

SUMMARY

Some embodiments relate to a method of implanting a prosthesis to repair a joint. The method includes displacing a first bone from the joint formed by an intersection between the first bone and a second bone. An end portion of the first bone is resected to define a resected end. A concavity is formed into the resected end using a shaping tool. The bone is compacted to form a support layer lining the concavity. The prosthesis is implanted in the concavity against the support layer without attaching the prosthesis to the support layer, the prosthesis including a first surface and a second surface opposite the first surface, each of the first and second surfaces being substantially convex in shape. The joint is reformed with the prosthesis such that the prosthesis remains unattached to the support layer and the first and second bones articulate about the prosthesis.

Some embodiments relate to a bone recess forming tool. The tool includes a forming head having a forming surface defining a convex hemispherical portion and an upswept portion extending beyond the convex hemispherical portion, the forming surface being adapted to form a recess into a bone.

Still other embodiments relate to a surgical kit of parts for implanting joint prostheses available in a plurality of graduating diameters. The kit includes a plurality of test prostheses each graduating in diameter such that each one of the test prostheses has a diameter corresponding to one of the available graduating diameters of the joint prosthesis. The kit also includes a plurality of reamers each graduating in diameter such that each one of the reamers has a diameter corresponding to one of the available graduating diameters of the joint prosthesis. The kit also includes a plurality of compactors each graduating in diameter such that each one of the compactors has a diameter corresponding to one of the available graduating diameters of the joint prosthesis. Each one of the test prostheses, reamers, and compactors having the same diameter forms an operational tool set for implanting a joint prosthesis of the same diameter, and further wherein each of the test prostheses, reamers, and compactors include colored indicia indicating to which operational tool set a particular test prosthetic, reamer, and compactor belongs.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications, permutations, and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
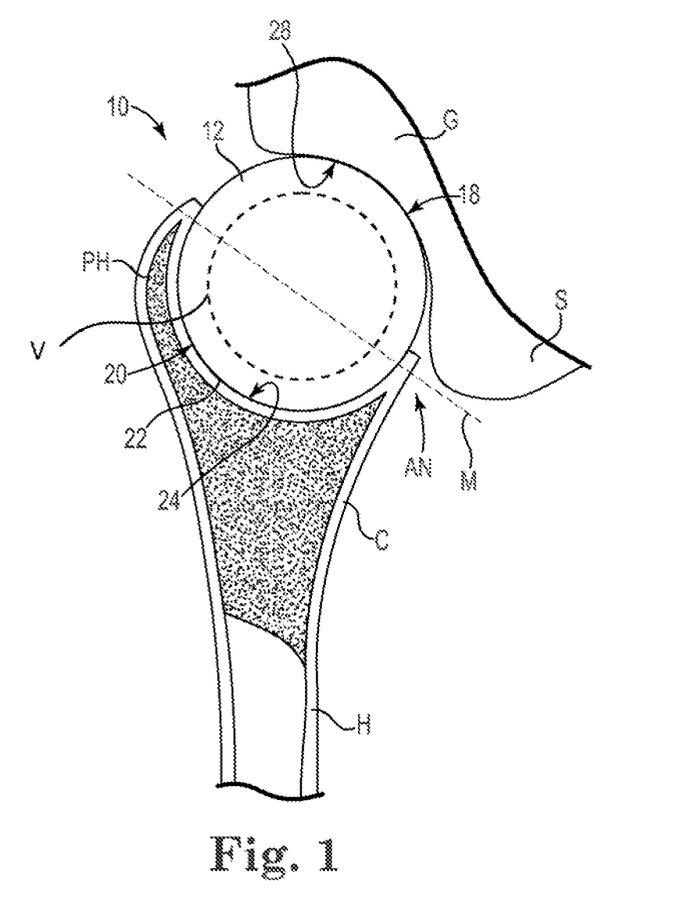
FIG. 1 shows a joint system, according to some embodiments.

FIG. 1 is a schematic view of a joint system 10 (e.g., a glenohumeral joint system) including an interpositional implant 12, a first boney structure, or bone (e.g., a humerus H) and a second boney structure, or bone (e.g., a glenoid G), where the first and second boney structures articulate about the interpositional implant 12. As shown in FIG. 1, in some embodiments, the interpositional implant 12 is interposed between the two boney structures—the humerus H and the glenoid G—to help repair joint function. Although the implant 12 is primarily discussed as being implanted in a human patient's shoulder, the implant 12 may also be modified and implanted in other locations. For example, the implant 12 is optionally modified to be implanted between a variety of boney structures in a hip, ankle, hand, foot, or other joint, for example, whether human or other animal.

Generally, the interpositional implant 12, also described as an interpositional prosthesis, is formed as a single piece, or monolithic unit, and includes at least two convex surfaces, although implants formed of separate, connected parts are contemplated. As shown, the implant 12 includes a convex first surface 18 and a convex second surface 20 opposed to the first surface 18, though the interpositional implant 12 is optionally non-spherical and the surfaces 18, 20 optionally have different radii of curvature from one other. As shown, the first surface 18 is in direct contact with the glenoid G, and in particular the glenoid cavity, and the second surface 20 is in direct contact with a portion of the humerus H.

Figure 2:
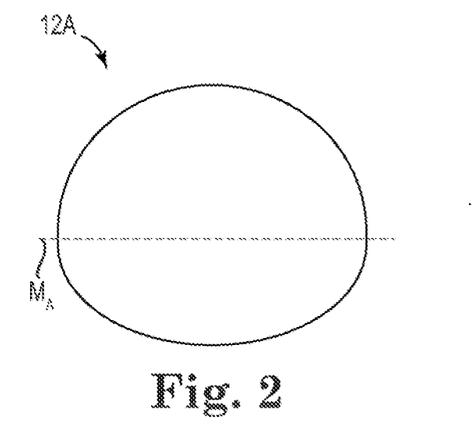
FIG. 2 shows an interpositional implant, according to some embodiments.
Figure 3:
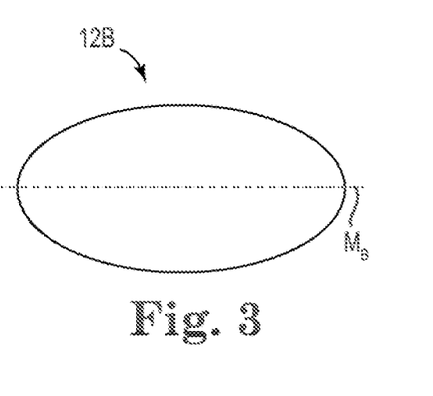
FIG. 3 shows another interpositional implant, according to some embodiments.

The implant 12 generally defines a midline M between the first and second convex surfaces 18, 20. For example, while FIG. 1 shows a generally spherical, or spheroid shape for the interpositional implant 12, while FIG. 2 shows an interpositional implant 12A having an upper, spheroid portion above a midline $M_A$ and a lower, spherical portion below the midline $M_A$ having a different radius of curvature. FIG. 3 shows an interpositional implant 12B having a more symmetrical spheroid shape (e.g., a prolate spheroid shape) above and below a midline $M_B$. In still other embodiments, the convexities of the first and/or second surfaces 18, 20 are complex, including multiple radii, including the shapes described in U.S. Patent Application Publication 2007/0225818, filed Mar. 21, 2007, and titled "Non-Spherical Articulating Surfaces in Shoulder and Hip Replacement," the entire contents of which are incorporated herein by reference for all purposes. Moreover, although some shapes for the implant 12 have been described, a variety of shapes are contemplated, such as an egg-shaped implant, for example.

In some embodiments, the interpositional implant 12 defines the midline M in an antero-posterior plane and a height perpendicular to the midline M, for example in a supero-inferior plane). In the case of a sphere, the diameter of the sphere corresponds to both the width of the implant 12 along the midline M and the maximum effective height of the sphere perpendicular to the midline M. The implant 12 is formed of an outer layer of pyrocarbon, or pyrolytic carbon, over a graphite substrate or is formed substantially entirely of pyrocarbon, for example. Some examples of pyrolytic carbon implants and associated use for joint repair are described in U.S. Pat. No. 6,436,146, filed Jan. 18, 2000, and titled "Implant for Treating Ailments of a Joint or Bone," the entire contents of which is incorporated herein by reference for all purposes. In some embodiments, the interpositional implant 12 is characterized by a Young's Modulus of from about 10 GPa to about 35 GPa, for example, or from about 21 to about 28 GPa, for example, which is relatively low compared to the much higher Young's modulus of titanium implants. The interpositional implant 12 is optionally hollow or otherwise defines an internal void V as indicated in FIG. 1 by a broken circle. Although a single, substantially spherical void, or internal hollow portion, is indicated the void V optionally takes a variety of shapes and forms, including multiple voids (e.g., a plurality of larger voids or a plurality of smaller voids similar to a sponge structure) or other forms. By including one or more voids, the weight of the implant 12 is optionally reduced and/or other properties of the implant 12 are adjusted as desired.

As shown in FIG. 1, the humeral head of the humerus H is removed, or resected, proximate the anatomical neck AN, where the humerus H defines a proximal humerus PH. The humerus defines a recess 22 that is substantially concave in shape, extending at least through a full hemispherical arc, although other shapes are also contemplated. The recess 22, also described as a concavity or a pocket, has an articulation surface 24, or reinforcement bed, that lines the recess 22 which, as described in greater detail below, is optionally formed via compacting and/or reaming methodology. The articulation surface 24 forms a reinforced bed, or liner, for contacting the interpositional implant 12. As described in greater detail, the recess 22 is formed into epiphyseal/metaphyseal bone of the humerus H and optionally extends into the diaphysis in some embodiments, though typically preferential to limit the recess 22 to the metaphyseal bone. Where the recess 22 extends into the diaphysis, or where the metaphyseal bone is thin or has degenerated, a plug or plugs (e.g., made of bone from the humeral head (not shown) or other bone material) are optionally used to reinforce any holes or weak spots in the articulation surface 24 produced during formation. In some embodiments, and as described in greater detail below, the articulation surface 24 is formed of cortical or cortical-like bone C that forms over time following surgical insertion of the interpositional implant 12. Generally, the depth of the recess 22 is measured or otherwise evaluated from the bottom of the recess 22 to a plane of the resected end of the humerus H, although other reference planes are employed as appropriate.

Generally, the interpositional implant 12 is not cemented, adhered, or otherwise fixed to the articulation surface 24, leaving the interpositional implant 12 free to rotate in the recess 22. In some embodiments, however, there is some frictional engagement between the recess and the interpositional implant 12—for example, in association with press fitting the interpositional implant 12 into the recess 22 and/or following growth of the humerus H.

The glenoid G defines an articulation surface 28 and, in some embodiments, the articulation surface 28 corresponds to the natural glenoid cavity where no or very little surface modification is made to the glenoid cavity during implantation. Use of the implant 12 with an unmodified glenoid cavity can be particularly beneficial for partial replacement of a shoulder joint in cases where the rotator cuff is still functional. In other embodiments, the articulation surface 28 is formed into the scapula S at the glenoid cavity (e.g., using the reaming and/or compacting methodology similar to that used with the humerus H (described in greater detail below) or a glenoid component is attached to the glenoid G for interacting with the implant 12 as shown in FIG. 4.

As shown in FIG. 1, and as discussed in greater detail below, the interpositional implant 12 optionally interacts directly with an articulation surface 28 of the glenoid G, e.g., without any intermediate components between the interpositional implant 12 and the glenoid cavity. In some embodiments, and as shown in FIG. 1, the interpositional implant 12 also interacts directly with the articulation surface 24, which is formed in the humerus H according to some methods of preparing the humerus H for receiving the interpositional implant 12.

Figure 4:
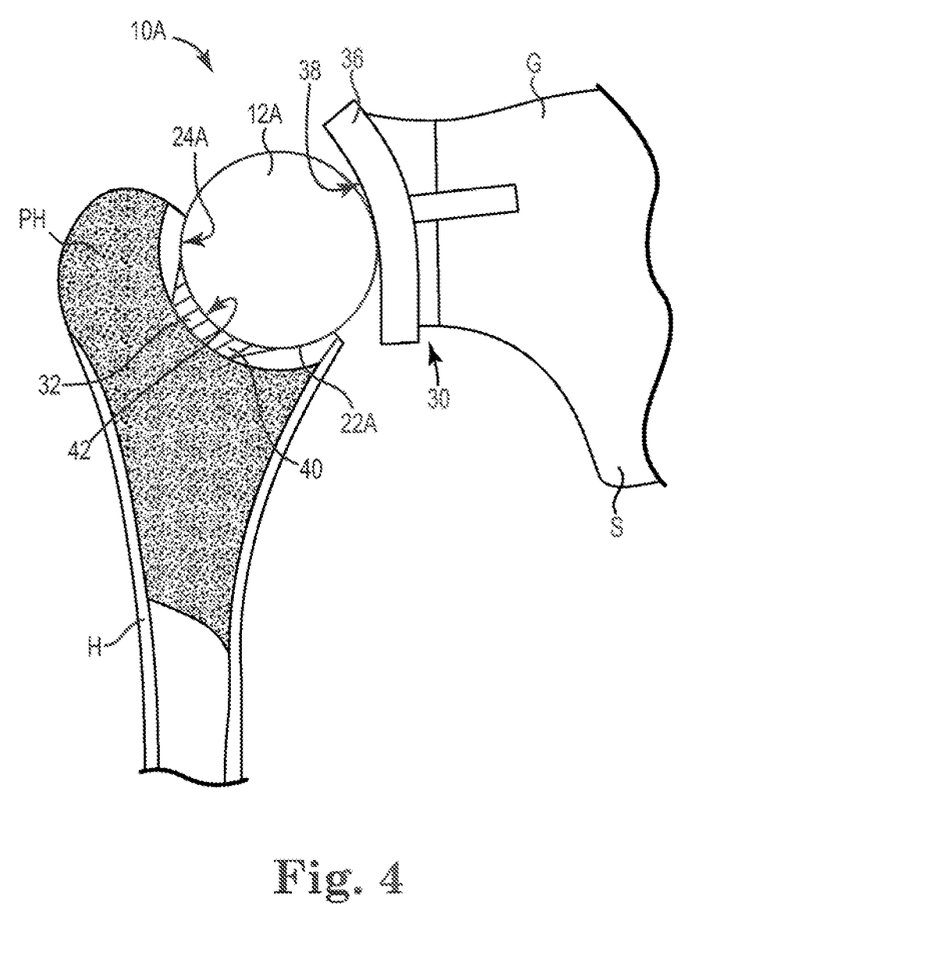
FIG. 4 shows another joint system, according to some embodiments.

In other embodiments, and as shown in FIG. 4, a joint system 10A further includes one or both of a glenoid component 30 (e.g., implanted in a scapula S of the glenoid G) and/or a humeral component 32, such as those described in U.S. Patent Application Publication 2009/0287309 ("the '309 Publication"), filed Dec. 17, 2008, and titled "Intra-Articular Joint Replacement," the entire contents of which is incorporated herein by reference for all purposes.

The glenoid component 30 includes an articular member 36 with a generally concave articular surface 38 that engages interpositional implant 12A, where the interpositional implant 12A is optionally substantially similar to the implant 12 and is laterally remote from the resected surface of the glenoid G in the sense that, if the articular member 36 were omitted, the interpositional implant 12A would be directly juxtaposed with the glenoid G (e.g., as is shown in the system 10 of FIG. 1).

The humeral component 32 optionally supplements, or reinforces, a recess 22A in the humerus H, where the recess 22A defines articulation surface 24A substantially similar to articulation surface 24. The humeral component 32 optionally includes an articular member 40 with a generally concave surface 42 formed from a resected portion of the humerus H and installed in the recess 22A according to similar methodology to that described in the '309 Publication, for example. Where both the glenoid and humeral components 30, 32 are present, the interpositional implant 12A is positioned between the articular member 36 of the glenoid component 30 and the articular member 40 of the humeral component 16A—the radius of the interpositional implant 12A being typically equal to or less than the radii of the concave articular surfaces 38, 42.

Figure 5:
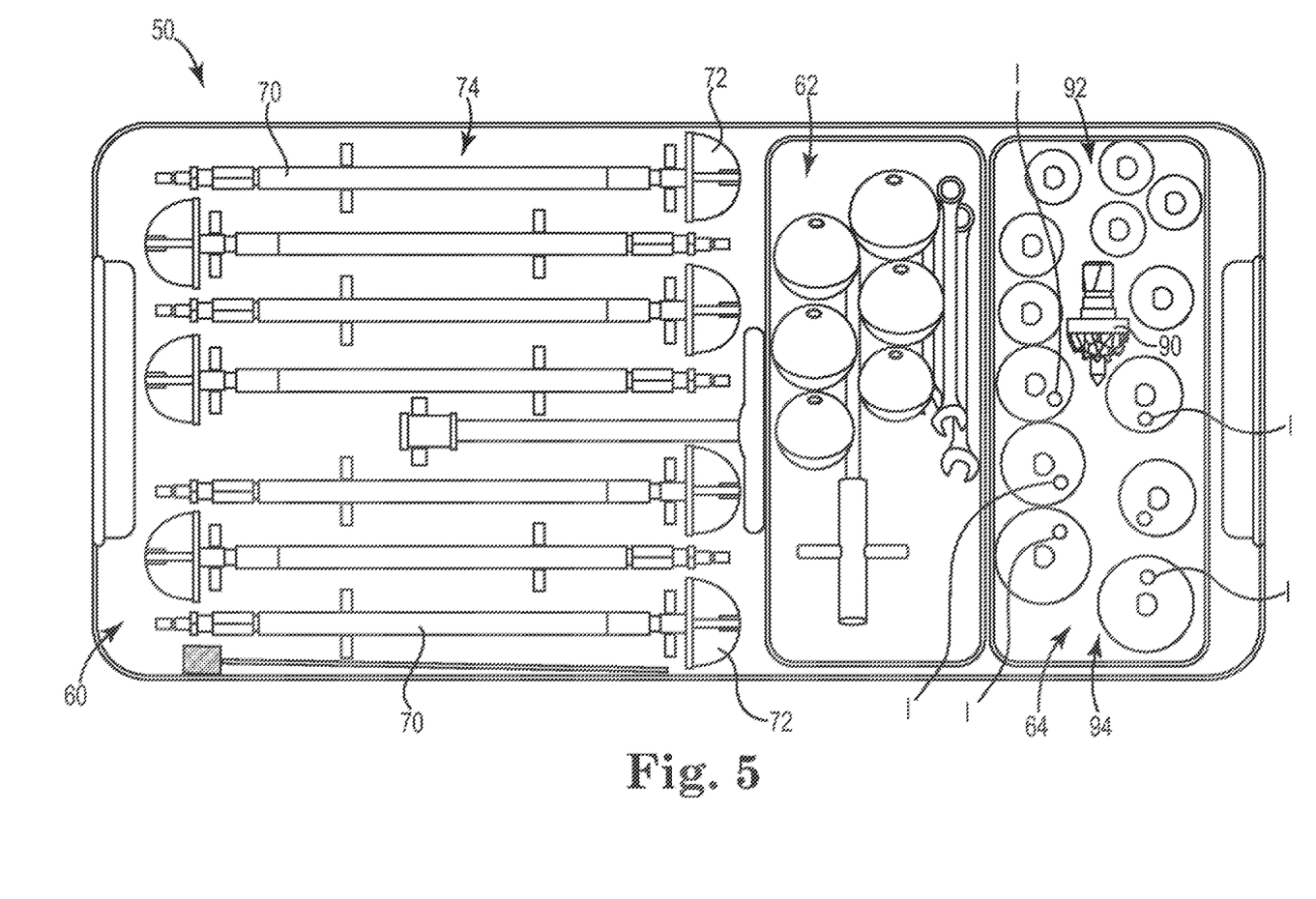
FIG. 5 shows a surgical kit, according to some embodiments.

FIG. 5 illustrates a surgical kit 50, or kit of parts, used in association with some surgical methods for implanting the interpositional implant 12. The kit 50 includes a plurality of reamers 60, a plurality of test implants 62, and a plurality of compactors 64. The kit 50 also optionally includes wrenches, pilot hole tips/bits, cleaning tips/bits, and other components as desired. In some embodiments, the kit 50 is prepackaged as a sterile unit and/or is adapted to be sterilized prior to use (e.g., via autoclave).

In some embodiments, the plurality of reamers 60 are described as forming or shaping tools and are provided in graduating sizes. The plurality of reamers 60 are generally indicated for use in preparing the recess 22 in the resected end of the humerus H. Each of the plurality of reamers includes a shaft 70 and a cutting head 72. In some embodiments, one of the plurality of reamers 60 is a starter reamer 74 having a smaller cutting head diameter than the other reamers 60. The starter reamer 74 is optionally utilized early in the formation process of the recess 22 in order to form initial cuts into the resected head of the humerus H, for example. In some embodiments, the starter reamer 74 is cannulated and includes an optional pilot tip (not shown), such as a sharp thin projection inserted into the cannulated reamer and projecting from the reamer tip to guide the reaming process. The reamers 60 are optionally adapted to have reaming diameters graduating in size from about 34 mm to about 46 mm (e.g., in 2 mm increments), although a variety of dimensions are contemplated.

Figure 6:
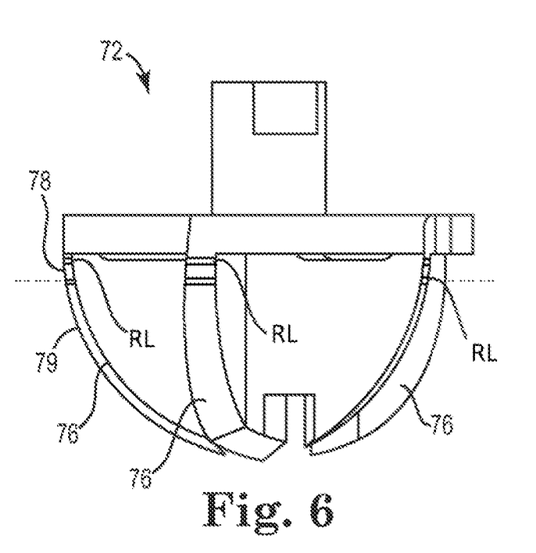
FIG. 6 shows a reamer of the surgical kit of FIG. 5, according to some embodiments.

Each shaft 70 is optionally color coded and/or otherwise marked with indicia (e.g., lettering) which, as described in greater detail, indicates whether a particular reamer 60 belongs to a corresponding operational tool set, where the tool sets are generally grouped by size (e.g., corresponding to an expected size for the implant 12 to be placed in the resected head of the humerus H). The cutting head 72 of one of the plurality of reamers 60 is shown in FIG. 6, according to some embodiments. Each of the reamers 60 is optionally substantially similar other than differing generally in reaming diameter, and as such the cutting heads of the plurality of reamers 60 are described collectively with reference to the head 72 shown in FIG. 6.

As shown in FIG. 6, the head 72 is generally dome-shaped and includes a plurality of arcuate blades 76, the profiles of which define a cutting or forming surface. In particular, the head 72 has a substantially convex outer profile such that the head 72 is adapted to cut, or carve a generally concave recess into bone, e.g., into the resected head of the humerus H. The convex outer profile of the cutting head 72 extends at least through a full hemispherical arc that defines a reaming diameter of the cutting head 72. In some embodiments, the head 72 is adapted to cut at least a full hemisphere and optionally includes an extended cutting portion 78 sweeping upward beyond a hemispherical cutting portion 79 of the cutting head 72. By extending the diameter of cut to a full hemisphere or more, the head 72 is adapted to form fully hemispherical recesses and recesses deeper than the diameter of cut of the cutting head 72. In some embodiments, the extended cutting portion 78 includes one or more demarcation lines RL for indicating one or more selected reaming depths (two are shown in FIG. 6, though more or less are employed as appropriate). In some embodiments, a first one of the demarcation lines RL is located approximately at a height corresponding to the transition from the hemispherical cutting portion 79 to the extended cutting portion 78 and a second one of the demarcation lines RL is located a pre-determined height above the first demarcation line RL, although a variety of heights are contemplated. As shown, the demarcation lines RL are optionally grooves formed into the blades 76 that are adapted or otherwise configured to be viewed by a surgeon during reaming.

Figure 7:
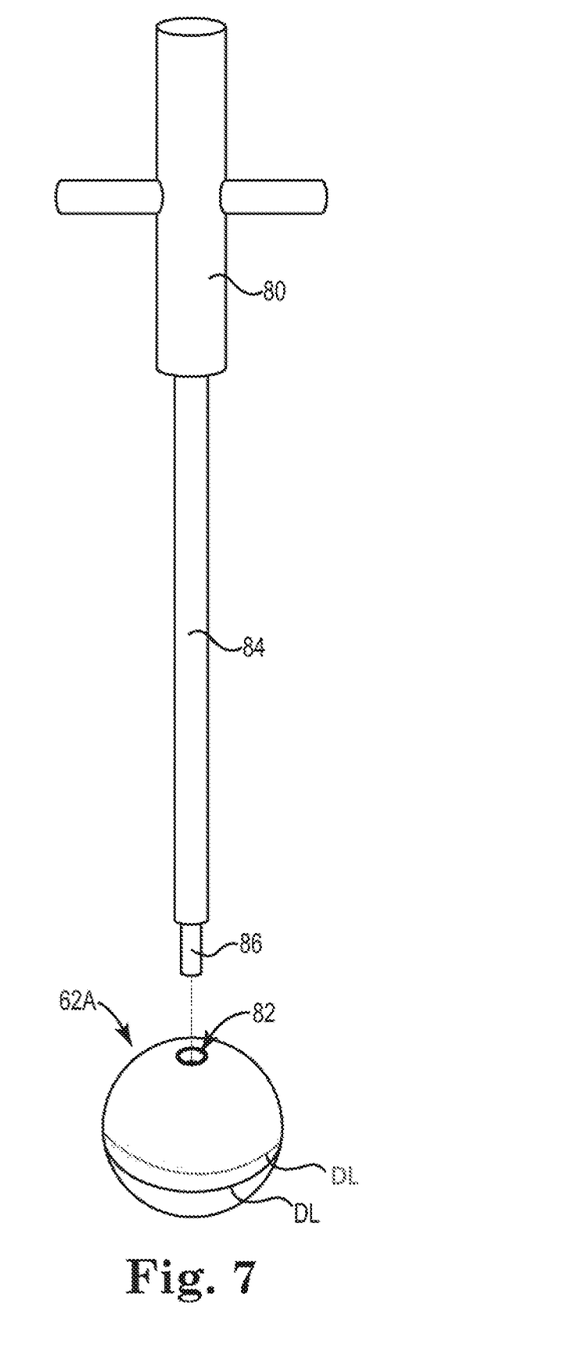
FIG. 7 shows a test implant and handle of the surgical kit of FIG. 5, according to some embodiments.

FIG. 7 shows a first test implant 62A of the plurality of test implants 62 along with an associated handle 80 for manipulating the test implants 62. In some embodiments, each of the test implants 62 is substantially similar other than differing generally in size and color, and as such the test implants 62 are described collectively with reference to the first test implant 62A shown in FIG. 7. Though the test implants 62 are shown as being substantially similar, it should be understood that test implants of differing shape, material, or other characteristic(s) are also contemplated.

As shown, the first test implant 62A is substantially spherical, or spheroid, and has one or more test depth lines DL. In some embodiments, a first one of the test depth lines DL is located approximately at a height corresponding to an equator of the first test implant 62A and a second one of the test depth lines DL is located a pre-determined height above the first test depth line DL, although a variety of heights are contemplated. Although two test depth lines DL are shown in FIG. 7, a greater or fewer number are contemplated as appropriate. As referenced above, the first test implant 62A is optionally color coded and is made of a material that is suitable for being temporarily implanted to check whether the implant 12 will perform as desired. The first test implant 62A also includes a receptacle 82 for securing the first test implant 62A to the handle 80. For example, the receptacle 82 optionally includes female threads for mating with the handle 80. In some embodiments, the test implants 62 having diameters graduating in size similar to the size selections available for the implant 12, for example from about 36 mm to about 46 mm (e.g., in 2 mm increments), although a variety of dimensions are contemplated.

As shown, the handle 80 includes an elongate shaft 84 terminating with a tip 86 suitable for connecting to the test implants 62. For example, the tip 86 is optionally provided with male threads for securing the tip 86 to receptacles in the test implants 62, such as the receptacle 82 in the first test implant 62A.

In some embodiments, the plurality of compactors 64 are described as forming or shaping tools and are provided in graduating sizes. Though generally used to form a compacted, more structurally sound surface, the compactors 64 are also optionally used to break up and remove pieces of bone as appropriate. In some embodiments, the plurality of compactors 64 include a starter compactor 90 (FIG. 8) with an optional pilot tip, a plurality of initial compactors 92 (such as the one shown in FIG. 9), and a plurality of final compactors 94 (such as the one shown in FIG. 10). As described further, and according to some methods, the starter compactor 90 is optionally used to begin the compacting process, one or more of the initial compactor 92 are used to continue the compacting process, and one of the final compactors 94 is used to finalize the recess 22 into a suitable depth and form for receiving the implant 12.

Figure 8:
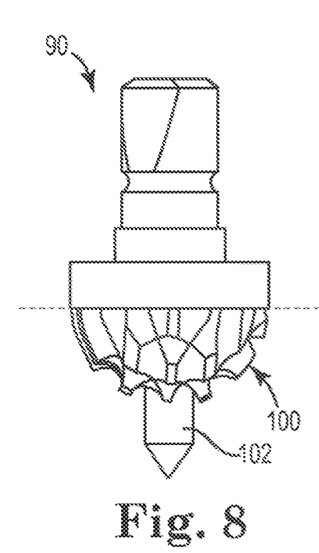
FIG. 8 shows a starter compactor of the kit of FIG. 5, according to some embodiments.

The starter compactor 90 shown in FIG. 8 has a convex compacting surface 100, also described as a forming surface, that extends through a hemispherical arc and is adapted to break up and compact bone (e.g., cancellous or spongy bone) as it forms a substantially concave cavity. As shown, the convex compacting surface 100 is generally equal to a full hemisphere in shape as designated by the broken line in FIG. 8, although the compacting surface 100 is optionally extended beyond a full hemispherical shape. For example, in some embodiments the compacting surface 100 is continued to sweep beyond a hemispherical shape. As shown, the starter compactor 90 optionally includes a pilot tip 102 to help ensure an accurate starting point for forming the recess 22. In some embodiments, the starter compactor 90 is adapted to have a forming/compacting diameter of about 20 mm, although a variety of dimensions are contemplated.

The initial compactors 92 graduate in size and, through an iterative process, can be used to progressively form a larger and larger compacted recess into the resected end of the humerus H. The initial compactors 92 are optionally substantially similar other than differing generally in size, and as such the initial compactors 92 are described collectively with reference to a first initial compactor 92A shown in FIG. 9. In some embodiments, the initial compactors 92 are adapted to have forming/compacting diameters graduating in size from about 22 mm to about 34 mm (e.g., in 2 mm increments), although a variety of dimensions are contemplated.

Figure 9:
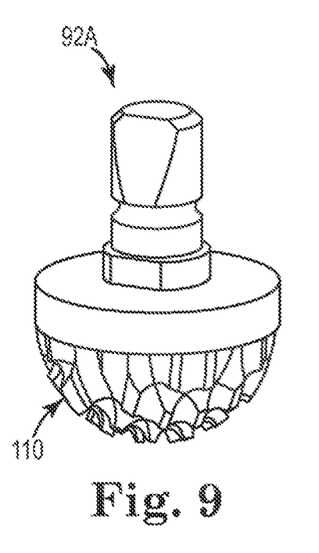
FIG. 9 shows an initial compactor of the kit of FIG. 5, according to some embodiments.

The first initial compactor 92A has a compacting surface 110 adapted to break up and compact bone (e.g., cancellous or spongy bone) as it forms a substantially concave cavity with the compacting surface 110. Similarly to the starter compactor 90, the convex compacting surface 110 is equal to a full hemisphere in shape, although other configurations are contemplated. For example, in some embodiments the compacting surface 100 is continued and sweeps beyond the fully hemispherical shape.

The final compactors 94 also graduate in size and are each optionally color coded to a corresponding one of the reamers 60 and test implants 62 forming one of the operational sets. For example, as shown in FIG. 5, each of the final compactors 94 includes indicia I, such as a colored dot, for indicating to which operational set the compactor 94 belongs. The final compactors 94 are optionally substantially similar other than differing generally in size, and as such the final compactors 94 are described collectively with reference to a first final compactor 94A shown in FIG. 10. In some embodiments, the final compactors 92 are adapted to have forming/compacting diameters graduating in size from about 36 mm to about 46 mm (e.g., in 2 mm increments), although a variety of dimensions are contemplated.

Figure 10:
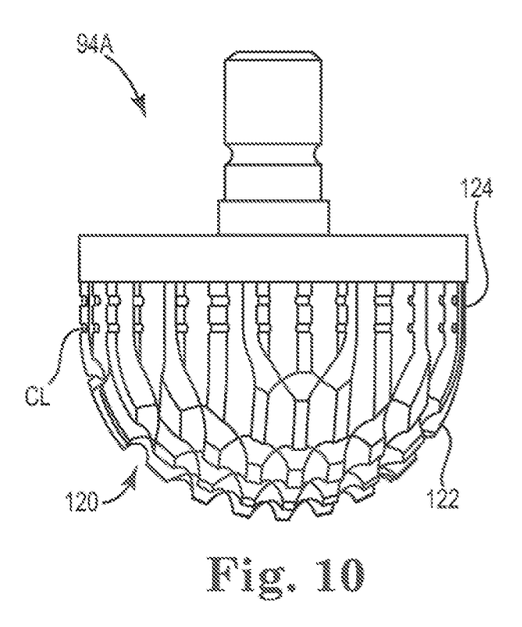
FIG. 10 shows a final compactor of the kit of FIG. 5, according to some embodiments.

The first final compactor 94A has a compacting surface 120 adapted to break up and compact bone (e.g., cancellous or spongy bone) as it forms a substantially concave cavity with the compacting surface 120. As shown in FIG. 10, the compacting surface 120 defines a hemispherical portion 122 and an upswept portion 124, where the compacting surface is extended, sweeping upward along a substantially straight line beyond the hemispherical portion 122 through the upswept portion 124. In at least this manner, the compacting surface 120 is adapted to form/compact the recess 22 to a full hemisphere and to a depth greater than the forming/compacting diameter while helping ensure that substantially all, or at least a greater portion of, the articulation surface 24 is compacted and thereby reinforced for receiving the implant 12.

In some embodiments, the first final compactor 94A defines one or more visible demarcation lines CL (e.g., a groove or line in the compacting surface 120) at one or more predetermined heights from the bottom of the compacting surface 120 for delineating a desired forming/compacting depth at which to cease a compacting process. Although two demarcation lines CL are shown in FIG. 10, embodiments with greater or fewer demarcation lines are contemplated as appropriate. In some embodiments, the demarcation lines CL are provided in regular increments (e.g., 2 mm) for indicating a plurality of formation/compaction depths. In some embodiments, a first one of the demarcation lines CL is located approximately at a height corresponding to the transition from the hemispherical portion 122 to the upswept cutting portion 124 and a second one of the demarcation lines CL is located a pre-determined height above the first demarcation line CL, although a variety of heights are contemplated. Moreover, in some embodiments the demarcation lines RL, the test depth lines DL, and/or the demarcation lines CL are provided at corresponding heights to one another, such that a single operational set (described in further detail below) has a uniform set of depth markings on the tool used in a surgical joint repair/replacement procedure to form the recess 22 to a demarcated depth using the markings on the compactors 60 and reamers 64 and test the performance of the recess 22 to that depth using the markings on the test implant 62.

As referenced above, in some embodiments the reamers 60, test implants 62, and final compactors 94 graduate in size and are color coded and/or include indicia (e.g., writing) to group reamers 60, test implants 62, and compactors 64 into operational sets. For example, a single operational set is optionally designated by a single color, where the single operational set includes one of the reamers 60, one of the test implants 62, and one of the compactors 64. Table 1 that follows is provided as an illustrative example and shows diametrical reaming/forming/test dimensions corresponding to a plurality of graduating, color coded operational sets, according to some embodiments, although other dimensions, color coding, and/or other indicia are contemplated.

TABLE 1

Operational Sets

| Operational Set | Diameter | Compactor Coding | Reamer Coding | Test Implant Coding |
|---|---|---|---|---|
| 1 | 36 mm | Red | Red | Red |
| 2 | 38 mm | Yellow | Yellow | Yellow |
| 3 | 40 mm | Green | Green | Green |
| 4 | 42 mm | Blue | Blue | Blue |
| 5 | 44 mm | Grey | Grey | Grey |
| 6 | 46 mm | White | White | White |

In view of the foregoing, a surgeon or other user provided with the surgical kit 50 is able to quickly and reliably select an operational tool set for a particular implant size.

Some methods for implanting the interpositional implant 12 to form the joint system 10 are described below with reference to FIGS. 1-10 (previously discussed) and FIGS. 11-14 which are illustrative of a method of selecting an appropriate depth of implantation.

In some embodiments, a preoperative assessment of the existing (e.g., degenerated) joint system in the patient is performed. The preoperative assessment optionally includes using frontal and axillary radiographs, as well as CT scanning to evaluate orientation of the glenoid G, quality of bone stock in the humerus H and glenoid G, and any muscle degeneration of the rotator cuff, for example. Based upon the preoperative assessment, the surgeon makes an initial determination of the optimal size and/or shape of the implant 12. In some embodiments, the implant 12 is available in a variety of diameters, where the surgeon or other user initially selects from a plurality of sizes (e.g., such as 36 mm, 38 mm, 40 mm, 42 mm, 44 mm, and 46 mm diameter spheres, although a variety of dimensions are contemplated). From the foregoing, in some embodiments, each of the sizes has a corresponding operational set to be used during implantation, such as those shown in Table 1.

Exposure of the humerus H and glenoid G is optionally accomplished via any of a variety of techniques. In some embodiments, the surgical incision is made using a deltopectoral approach to the humerus H and glenoid G. The incision is made from a tip of the coracoid process and follows the deltopectoral groove. The upper part of the pectoralis major is optionally released to improve external rotation, the clavipectoral fascia is incised at an outer edge of the coracobiceps, and the acromioclavicular ligament is partially severed to facilitate exposure of the sub-scapular and circumflex vessels. The circumflex vessels are then ligated to achieve hemostasis during the entire surgical procedure. The axillary nerve is identified and protected. After the superior arthrotomy, the subscapularis is incised with the capsule to about an inch and a half of the bicipital groove at the neck anatomy. By raising the arm in adduction and external rotation and retropulsion, the humeral head is then dislocated forward. The anterior capsule is released from front to back, allowing the exposure of osteophytes. Ultimately, the humeral head is freed and displaced from the glenoid G and exposed for processing.

Figure 11:
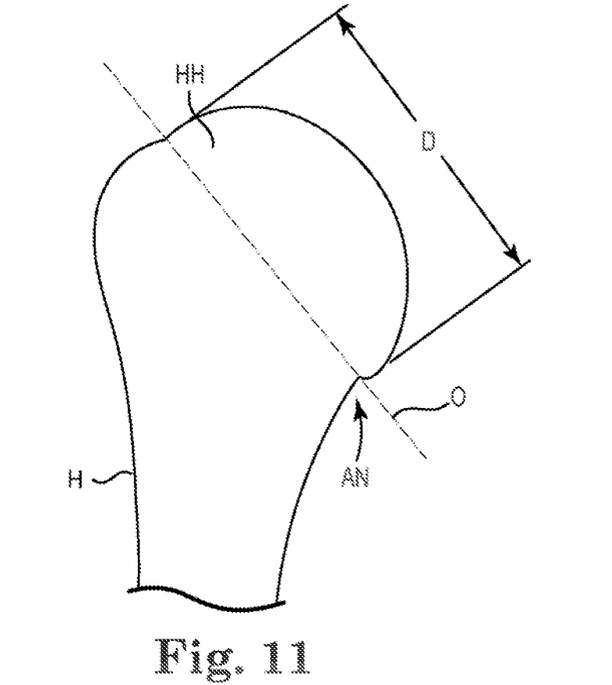
FIGS. 11-14 are illustrative of a method of implanting and forming the joint system of FIG. 1, according to some embodiments.
Figure 12:
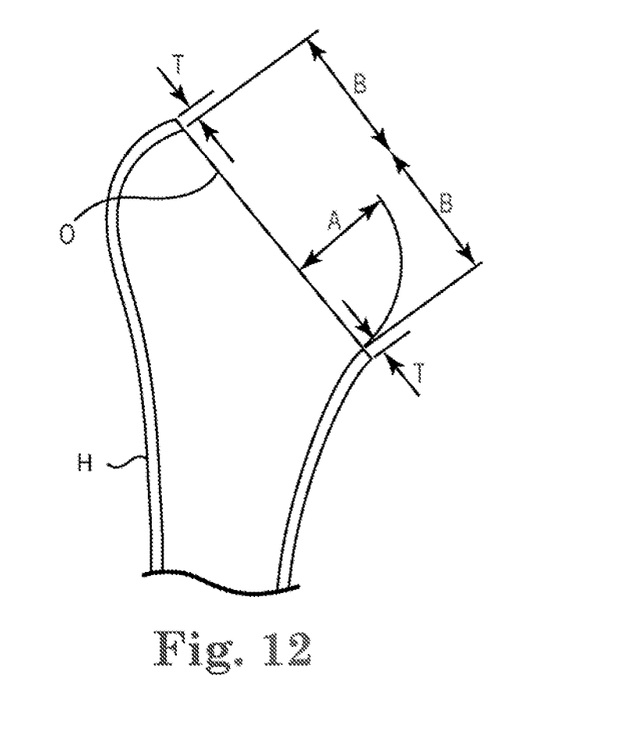

As indicated in FIG. 11, once dislocated, the humeral head HH is resected (e.g., at the anatomical neck AN) to form a resected end defining a resection plane O (FIG. 12). Transverse dimensions of the anatomical neck AN or the resected humeral head are then measured using calipers or other measuring tool in at least two planes to assess the size of implant use. In some embodiments, the two planes are generally perpendicular to one another, such as the anteroposterior and superoinferior planes. In some embodiments, where the measurements along the planes are different from one another, the smallest of the measurements is selected as the humeral head size. In some embodiments, the implant size is either initially selected or is confirmed to be about 2 mm to about 4 mm below the humeral head size.

In order to determine a depth at which the implant 12 is to be installed (or alternatively, to what depth the recess 22 should be formed), the smallest of the resected end measurements is selected as the initial resected end diameter D.

Figure 13:
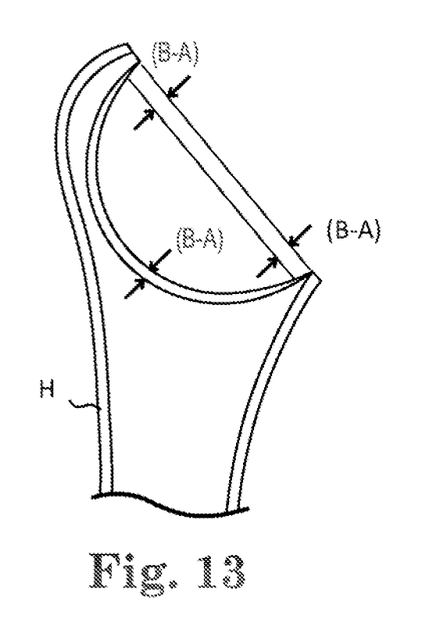
Figure 14:
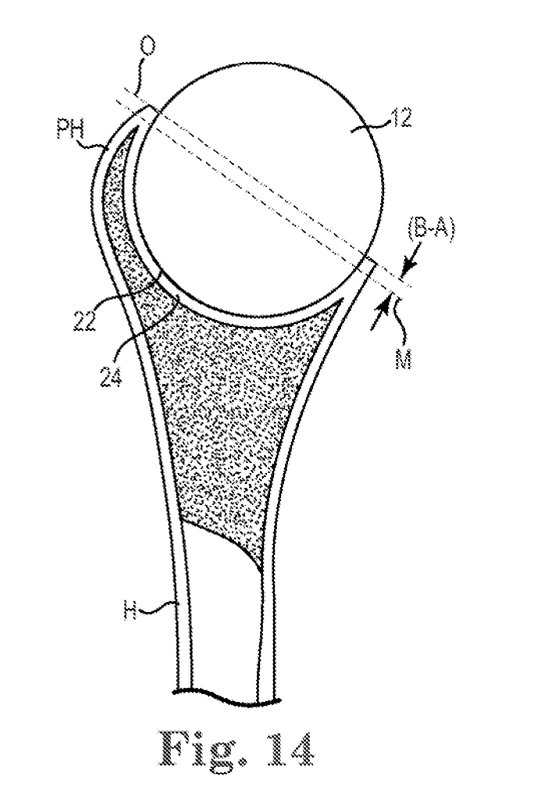

As shown in FIG. 12, based upon empirical or other data, the resected end diameter D is correlated to a predicted projection height A, also described as a desired projection height A, of the implant 12 above the resection plane O that will help ensure proper tensioning of the glenohumeral joint once the implant is received by the glenoid G and the joint has healed. For example, empirical data may be obtained relating to natural projection heights (i.e., in healthy joints) of the humeral head relative to humeral head diameter at the anatomical neck. A thickness of the cortical bone at the resection plane O is either estimated via empirical data or is directly measured using any of a variety of techniques (e.g., using a micrometer, radiographs, and others). In some embodiments, the implant diameter (and, therefore implant radius B) is selected by subtracting the thickness T of the cortical bone from the end diameter D (D−(2×T)=implant diameter). As shown in FIGS. 12 and 13, generally, the radius B of the implant 12 is greater than the predicted projection height A, such that B minus A equals the depth the midline M of the implant 12 is preferably pushed down with respect to the resection plane O in order to help ensure the surface of the implant 12 projecting from the recess 22 is well-positioned for proper tensioning of the joint as shown in FIG. 14. In terms of implant height, the depth the midline M is depressed with respect to the resection plane O is one-half the implant height minus the predicted projection height A.

In some embodiments, after a diameter of the implant 12 is selected and the depth of the recess 22 is determined, the recess 22 is formed according to a reaming and compacting process. With the implant diameter known, the surgeon selects the corresponding operational set (one of the reamers 60, one of the test implants 62, and one of the compactors 64) for forming the recess 22.

The reaming and compacting processes are generally used iteratively to form the recess 22 with an adequate depth. As previously referenced, the reamers 60 are well suited to forming a fully hemispherical and/or deeper shape for the recess 22 (in comparison to traditional reamers that terminate the cutting surface prior to a full hemisphere).

Similarly, the compactors 64 are also well suited to forming fully hemispherical recesses and/or deeper recesses. In some embodiments, the visible demarcation on each of the final compactors 94 (e.g., visible demarcation CL) corresponds to the desired depth to which the recess is to be formed and compacted relative to the resection plane O, which, in some embodiments is greater than the radius B of the implant 12 by an amount corresponding to the implant radius B minus the predicted projection height A. Using the visible demarcations, such as demarcation CL, a surgeon performing the compacting process is readily able to visualize when the desired recess depth has been achieved.

The compacting process is particularly useful to reinforce the articulation surface 24. For example, compacting helps artificially densify the spongious metaphyseal bone, building a stronger lining or floor to receive the implant 12. It has been surprisingly found that by using a relatively low Young's modulus for the implant 12 (e.g., low relative to titanium, for example), further bone densification of the articulation surface 24 is encouraged over time during operational loading, but without overly stressing the articulation surface 24. Eventually, the bone density at the surface 24 may approach that of the cortical bone of the humerus, as generally indicated in FIG. 14 by the continuous, white region on the exterior surface and recess 22 of the humerus H.

In some embodiments, compaction begins with the starter compactor 90 (e.g., being of 20 mm diameter). The starter compactor 90 helps initially center the recess 22 in the middle of the resection plane O and ensures that the recess 22 remains centered during ensuing compacting/reaming with larger diameter tools.

Compaction of the metaphyseal bone continues by gradually increasing the diameter of compaction with the initial compactors 92 until one of the final compactors 94 corresponding to the operational set that has been selected is used to form the recess 22 to its final, predetermined size. The starter compactor 90 and initial compactors 92 are generally only inserted to the depth of their respective compacting surfaces (e.g., only up to a single radial depth of cut) to help ensure that the recess 22 is not initially formed too deep. Thus, in some embodiments, each of the starter and initial compactors 90, 92 is inserted to the end of the cutting surface, which marks the height corresponding to a hemisphere. In some embodiments, this also helps avoid risk of humeral fracture during the initial compacting phases.

Once the recess 22 is sufficiently formed, the final compactor 94 of the selected operational set is used to form the recess 22 to the predetermined depth by compacting the articulation surface 24 with the final compactor 94 until the demarcation line is generally parallel with the resection plane O. If, during the process, it appears that the final compactor 94 will contact the external cortical bone, or if the final compactor 94 actually begins to contact the cortical bone, the surgeon optionally switches to a smaller diameter for the implant 12.

Additionally, where the quality of the metaphyseal bone is poor, the surgeon optionally strengthens the articulation surface 24 during compaction by packing pieces of bone grafts taken from the humeral head into the recess 22. Depending on the quality of the bone in the humerus H, the compacting and reaming process can lead to an opening on the medullary canal at the bottom of the newly-created articulation surface 24. In some embodiments, the surgeon blocks or plugs such an opening with a plug material (e.g., a cement or bone slurry) or using a plug built using the resected head (e.g., similar to the articular member 36 of the joint system 10A shown in FIG. 4).

Alternatively, if the cancellous bone is dense and inhibits satisfactory preparation of the recess 22, the reamers 60 are used to mill/ream the recess 22, where reaming stops once the reamer 60 has been inserted to the full hemispherical depth of the cutting surface of the reamer 60. Where reaming is needed, the recess 22 is prepared by starting with a smaller reamer diameter (e.g., 34 mm) and gradually increasing the reamer diameter up to the selected diameter of the implant 12. As previously mentioned, reaming and compaction are optionally used interchangeably by the surgeon until a satisfactory depth for the recess 22 is achieved and the articulation surface 24 is in an acceptable state.

Once the recess 22 has been formed as desired, the test implant 62 of the selected operational set is selected. For example, using the color coding previously mentioned, the test implant 62 of the same color as the final reamer 60 and final compactor 64 is used. The test implant 62 is assembled onto the handle 80. The test implant 62 is then introduced in the recess 22. The test depth lines DL of the test implant 62 help the surgeon visualize whether the test implant 62 has been sufficiently inserted into the recess 22 and, in turn, whether the recess 22 is formed to a sufficient depth. The test implant 62 is then placed into contact with the glenoid G to allow articulation about the test implant 62. Stability and mobility testing is performed by physically manipulating the humerus. During testing the handle 80 is optionally removed to facilitate freedom of movement and later resecured to the test implant 62 for removal thereof from the recess 22. During the stability and mobility testing, the surgeon verifies there is no gleno-humeral impingement or impingement between the humerus and the acromion.

The test implant 62 is removed after testing with the aid of the handle 80. If the surgeon perceives too much tension in the muscles or articulation of the joint appears particularly tight, a smaller test implant 62 is and/or a smaller size of the implant 12 is selected or the surgeon optionally attempts to depress the test implant 62 further into the recess 22 and/or depress the implant 12 further into the recess upon implantation thereof. If the surgeon perceives insufficient tension in the muscles and/or in the case of gleno-humeral impingement, a larger size for the test implant 62 and/or implant 12 can be selected instead, with additional compacting/reaming steps as appropriate.

Once the testing is completed to the surgeon's satisfaction, the implant 12 of the selected size (typically of the same diameter as the test implant 62) is then selected and introduced into the recess 22. In some embodiments, where the implant 12 is formed of pyrocarbon, for example, it is important that the surface of the implant 12 not be maned or otherwise damaged. For example, the implant 12 should not be impacted into place in the recess 22. The implant 12 is not cemented or otherwise fixed in the recess 22 according to some embodiments. The joint is reformed with the implant 12 in place, for example, according to the general methodology that follows.

The scapula S is repaired tendon-by-tendon as necessary and the aid of bone sutures secured to the humerus are used as needed. Where fixed to the humerus, the tendon is optionally displaced medially to promote recoupration and external rotation. Wound closure proceeds step-by-step in a traditional manner and the arm can be immobilized with a sling, for example. Generally, the same post operatives are recommended to that of a total prosthesis joint replacement (e.g., non-strenuous exercise and work resumed the first day after surgery with a sufficient waiting period before increased stretching/movement of the joint).

Various modifications, permutations, and additions can be made to the exemplary embodiments and aspects of the embodiments discussed without departing from the scope of the present invention. For example, while the embodiments describe concave articular surface above refer to particular features, the scope of this invention also includes embodiments having different combinations of features and embodiments that do not include all of the features. Accordingly, the scope of the present invention is intended to embrace all such alternatives, modifications, permutations, and variations as fall within the scope of the claims, together with all equivalents thereof.

What is claimed is:

1. A method of repairing a joint, the method comprising:
   exposing a first bone of the joint;
   resecting an end portion of the first bone to form a resected end defining a resection plane;
   forming a concavity in the resected end portion of the first bone using a shaping tool, the concavity extending at least through a full hemispherical arc;
   selecting a diameter of the prosthesis to be implanted; and
   implanting a prosthesis having the selected diameter in the concavity.

2. The method of claim 1, wherein forming the concavity comprises compacting the resected end portion of the first bone with a plurality of compactors having gradually increasing diameters.

3. The method of claim 1, wherein forming the cavity comprises shaping the resected end portion of the first bone until a demarcation line on the shaping tool is parallel with the resection plane.

4. The method of claim 3, wherein the demarcation line is at a position on the shaping tool that corresponds to a diameter of the prosthesis minus a predicted projection height of the prosthesis above the resected end that promotes adequate tensioning of the joint.

5. The method of claim 1, wherein forming the concavity comprises reaming the resected end portion of the first bone with a plurality of reamers having gradually increasing diameters.

6. The method of claim 1, wherein forming the concavity comprises iteratively compacting and reaming the resected end portion of the first bone.

7. The method of claim 1, further comprising selecting a test prosthesis based on a final shaping tool used to form the concavity.

8. The method of claim 7, further comprising selecting the test prosthesis having a same color as the final shaping tool.

9. The method of claim 7, further comprising introducing the test prosthesis into the concavity.

10. The method of claim 9, further comprising confirming the concavity is formed to a sufficient depth using depth lines on the test prosthesis.

\* \* \* \* \*